United States Patent [19]

Zimmerman et al.

[11] Patent Number: 4,582,802

[45] Date of Patent: Apr. 15, 1986

[54] STIMULATION OF ENZYMATIC LIGATION OF DNA BY HIGH CONCENTRATIONS OF NONSPECIFIC POLYMERS

[75] Inventors: Steven B. Zimmerman, Bethesda; Barbara H. Pheiffer, Takoma Park, both of Md.

[73] Assignee: The United States of America as represented by the Department of Health and Human Services, Washington, D.C.

[21] Appl. No.: 537,572

[22] Filed: Sep. 30, 1983

[51] Int. Cl.[4] .................. C12P 19/34; C12N 15/00; C12N 9/88

[52] U.S. Cl. .................. 435/91; 435/172.3; 435/232; 935/77; 935/101

[58] Field of Search .................. 435/6, 91, 172.3, 232; 935/77, 111

[56] References Cited

U.S. PATENT DOCUMENTS 4,264,731  4/1981  Shine .................................... 435/91
4,302,204  11/1981 Wahl et al. ........................... 435/6
4,321,365  3/1982  Wu et al. ............................. 435/91

OTHER PUBLICATIONS

Griffith, "Ligation of Nicked SV40 DNA in a Polyethylene Glycol-Condensed State as a Test for Net Coiling" Biopolymers 17(1) pp. 237-341 (1978).

Maniatis et al, "Molecular Cloning" Cold Spring Harbor Laboratory (1982) pp. 392-393.

Wahl et al, "Efficient Transfer of Large DNA Fragments from Agarose Gels to Diazobenzyloxymethyl-Paper and Rapid Hybridization by Using Dextran Sulfate" Proceedings of the National Academy of Sciences 76(8) pp. 3683-3687 (1979).

Zimmerman et al, "Macromolecular Crowding Allows Blunt-End Ligation by DNA Ligases from Rat Liver or *Escherichia coli*" Proceedings of the National Academy of Sciences 80 pp. 5852-5856 (1983).

Wetmur, "Acceleration of DNA Renaturation Rates" Biopolymers 14 pp. 2517-2524 (1975).

Lerman, "A Transition to a Compact Form of DNA in Polymer Solution", *Proc. Nat. Acad. Sci. USA* 68: 1886-1890 (1971).

Wieder, et al, "One Hundred-Fold Acceleration of DNA Renaturation Rates in Solution", *Biopolymers 20:* 1537-1547 (1981).

Minton, "Excluded Volume as a Determinant of Macromolecular Structure and Reactivity", *Biopolymers 20:* 2093-2120 (1981).

Primary Examiner—Thomas G. Wiseman
Assistant Examiner—John E. Tarcza
Attorney, Agent, or Firm—Holman & Stern

[57] ABSTRACT

DNA ligase activity is strongly accelerated in the presence of high concentrations of non-specific polymers, with an accompanying change in product distribution characteristics. The rate of blunt-end ligation of DNA substrate by T4 DNA ligase is particularly affected, with a product shift from closed circular species to linear oligomers. The method provides a way to increase the rate of enzymatic DNA ligation and the size of the linear products. It may be useful when preparing large amounts of polymers by ligation of oligomers or when ligating amounts of DNA or deoxyribooligomers so low in concentration that a reduced yield would otherwise result.

26 Claims, 14 Drawing Figures

BLUNT-ENDED LIGATION

LIGATION OF SINGLE-STRAND BREAKS (NICKS)

LIGATION OF COHESIVE ENDS

FIG. 1A BLUNT-ENDED LIGATION

FIG. 1B LIGATION OF SINGLE-STRAND BREAKS (NICKS)

FIG. 1C LIGATION OF COHESIVE ENDS

PEG, %: 0  0  3  5  7  9  11  13  15  17  19  25  27

FIG. 6B

PEG, %: 0  0  3  5  7  9  11  13  15  17  19  23  27

FIG. 7A

| Oligomer: | 6 8 10 12 | 6 8 10 12 | 6 8 10 12 |
| DNA Ligase: | — — — — | + + + + | + + + + |
| PEG: | — — — — | — — — — | + + + + |

FIG. 7B

| Oligomer: | 6 8 10 12 | 6 8 10 12 | 6 8 10 12 |
| DNA Ligase: | — — — — | + + + + | + + + + |
| PEG: | — — — — | — — — — | + + + + |

STIMULATION OF ENZYMATIC LIGATION OF DNA BY HIGH CONCENTRATIONS OF NONSPECIFIC POLYMERS

BACKGROUND OF THE INVENTION

The effect of macromolecular crowding on the kinetics and equilibria of biochemical reactions has been postulated to be of general significance (Minton, *Biopolymers* 20: 2093-2120, 1981). In vivo, these reactions occur in the presence of very high concentrations of non-specific background macromolecules termed "volume excluders", which do not appear to directly participate in the reaction, but which may theoretically affect the thermodynamic activity and conformational equilibria of a variety of reaction systems.

Consistent with this theory are a number of studies reporting an alteration of in vitro behavior of biological systems in the presence of high concentrations of polymers as volume excluders. Exemplary is the reported acceleration of renaturation of DNA in the presence of volume-excluding inert polymers (Wieder, et al, *Biopolymers* 20: 1537-1547, 1981), and the reported use of highly concentrated polymer solutions to effect a conformational change in DNA derived from $T_4$ and $T_7$ bacteriophage (Lerman, *Proc. Natl. Acad. Sci.* 68: 1886-1890, 1971).

SUMMARY OF THE INVENTION

It has now been found that a more complete expression of enzymatic ligation of duplex DNA is possible with macromolecular crowding of the ligation medium. Ligation of DNA substrates is conventionally catalyzed by DNA ligases in dilute solution in vitro. The presence of volume excluding polymers in sufficiently high concentration in the ligation medium greatly accelerates DNA ligase activity, and product distribution characteristics differ markedly. Further, DNA ligases which show little or no blunt-end ligation activity in dilute solutions are active in the volume-occupied solutions of the present invention.

The invention thus provides an improved method for enzymatic ligation of DNA duplexes through which the ligation reaction rates and product characteristics may be controlled. Increased reaction rates of up to about 1000-fold and increased product size of 10-fold or more are demonstrated; the increased productivity of the ligation method of the invention has significant potential for recombinant DNA applications.

FIGURE LEGENDS

FIG. 1. Ligation of different arrangements of strand-breaks in double-stranded DNA.

In contrast to the substrate for blunt-end ligation (A), the strands which are joined at single-strand breaks (B) or adhered cohesive ends (C) are held in apposition by complementary base-pairing interactions between the strands. The sites of ligation are structurally indistinguishable from the rest of the backbone, although here marked by closed circles for emphasis.

Figure 2:
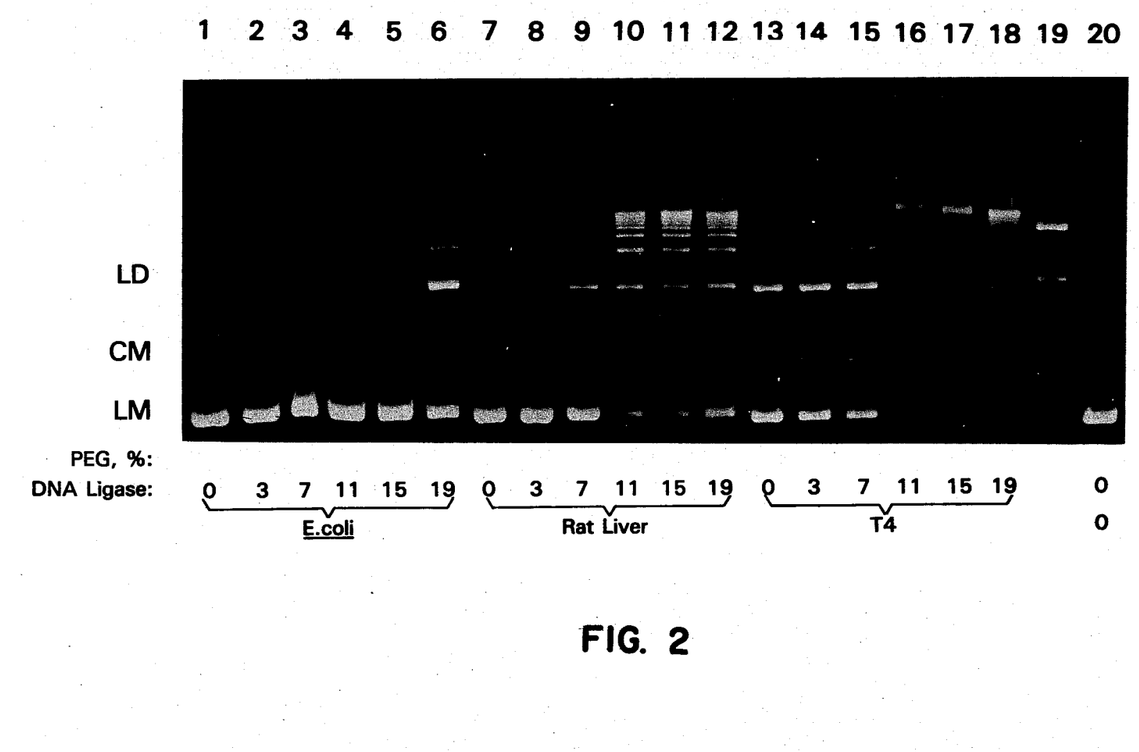
FIG. 2 is a gel electrophoretic pattern illustrating the effect of PEG 6000 on blunt-end DNA ligation by several DNA ligases.

FIG. 2. Effect of PEG 6000 on blunt-end DNA ligation by *E. coli*, rat liver, or T4 DNA ligases.

*E. coli*, rat liver, T4, or no DNA ligase was added as indicated (0.45 μl of *E. coli* ligase Fraction VII, 9 μl of rat liver ligase Fraction IV or 3.75 units of T4 ligase). PEG 6000 was present at the indicated (w/v) concentrations. Incubation (30 μl) was at 20° for 4 hours for lanes 1-6 and 1 hour elsewhere. HindIII endonuclease-digested λ DNA was added to lane 19. LM, linear monomer; CM, circular monomer; LD, linear dimer.

Figure 3:
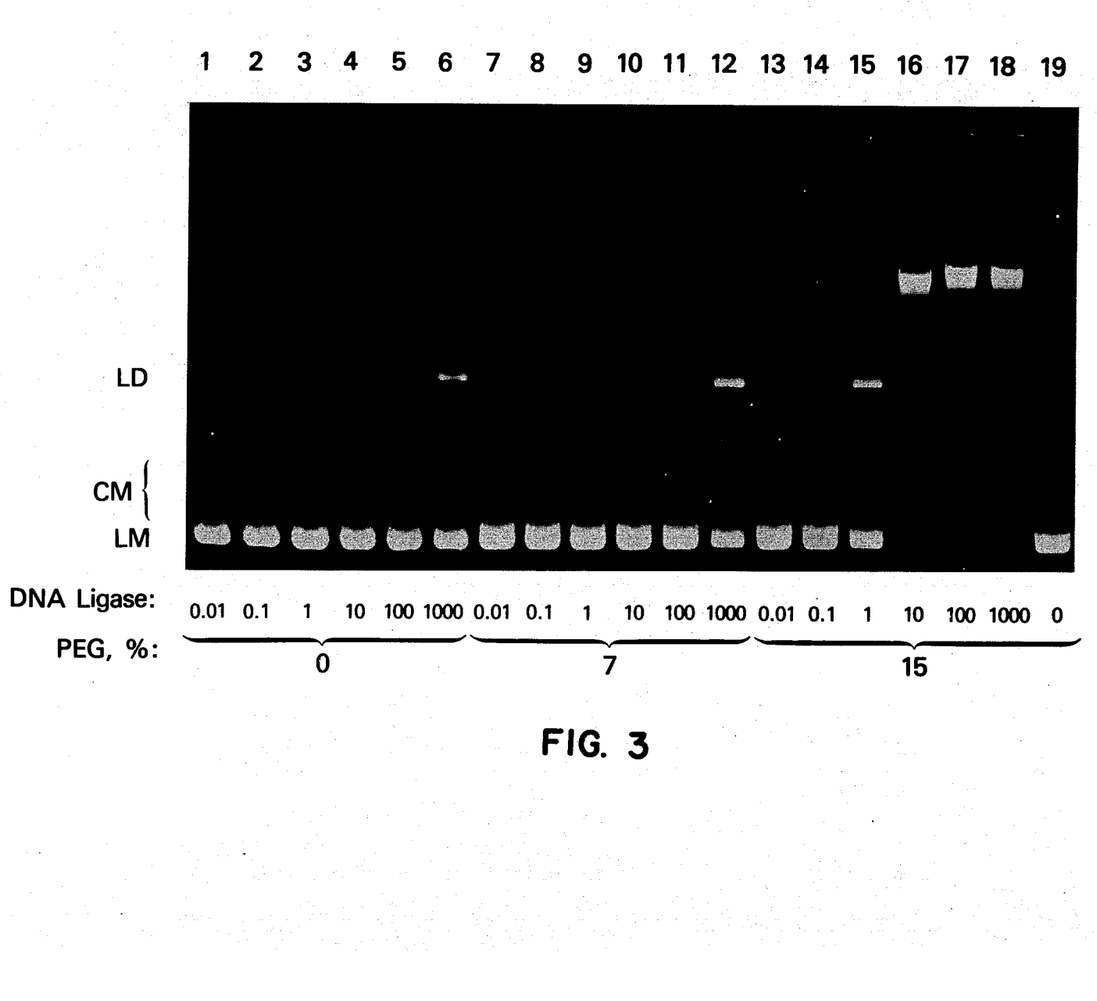
FIG. 3 is a gel electrophoretic pattern illustrating the effect of PEG 6000 on the blunt-end ligation of DNA as a function of T4 DNA ligase concentration.

FIG. 3. Effect of PEG 6000 on the blunt-end ligation of DNA as a function of T4 DNA ligase concentration. Ligase reaction mixtures as in Methods with the PvuII nuclease-digested DNA substrate, contained the indicated concentrations of PEG 6000 (w/v) and relative amounts of T4 DNA ligase ($1=2.5\times 10^{-3}$ units/assay). Gel, 0.8% agarose. LM, linear monomer; CM, circular monomers; LD, linear dimer.

Figure 4:
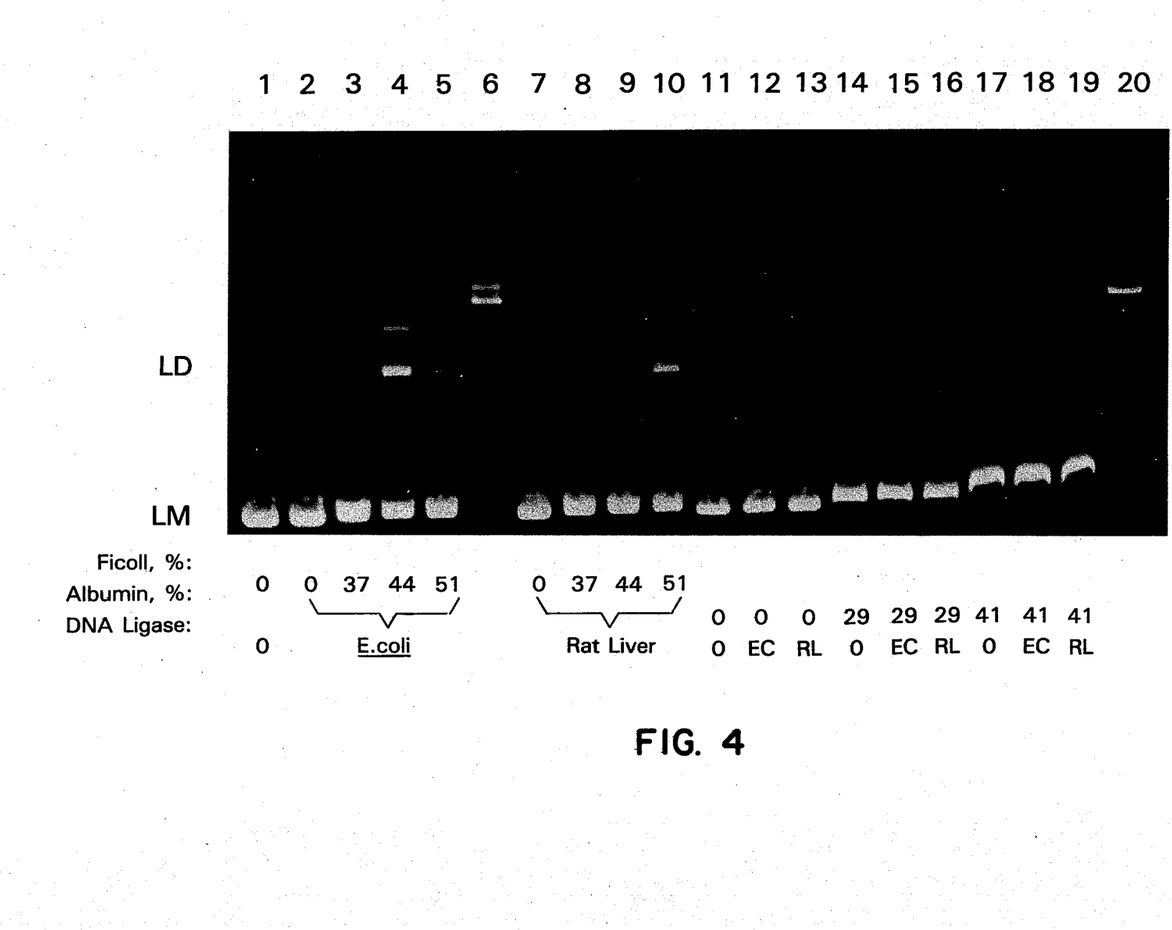
FIG. 4 is a gel electrophoretic pattern showing the effect of Ficoll 70 or BPA on blunt-end ligation of DNA by two DNA ligases.

FIG. 4. Effect of Ficoll 70 or bovine plasma albumin on blunt-end DNA ligation by *E. coli* or rat liver DNA ligases.

Ficoll 70 or bovine plasma albumin was present at the indicated (w/v) concentrations with *E. coli* ligase (0.45 μl of Fraction VII) or rat liver ligase (1.6 μl of Fraction IV). Samples for lanes 11-20 were diluted with an equal volume of 10 mM Tris HCL buffer, pH 8-0.1 mM EDTA before addition of Mixture A (see Methods) to minimize distortion of the electrophoretic pattern, Incubation (30 μl) was for 2 hours at 20° C. A mixture of HindIII endonuclease-digested λ DNA and λ DNA was added to lanes 6 and 20. EC, *E. coli*; RL, rat liver; LM, linear monomer; LD, linear dimer.

Figure 5A:
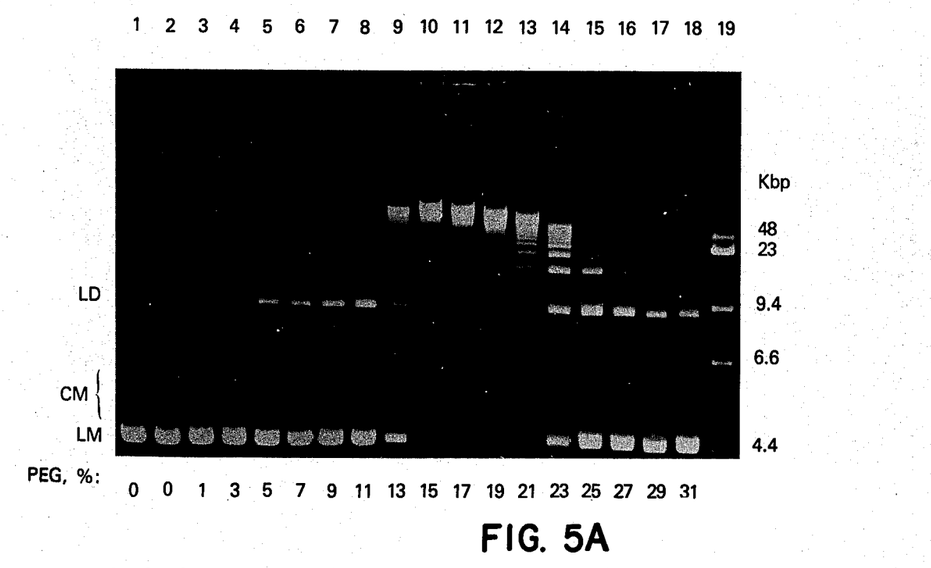
FIG. 5 is a gel electrophoretic pattern illustrating the effects of PEG 6000 concentration on blunt-end ligation of DNA by T4 DNA ligase on sedimentability.
Figure 5B:
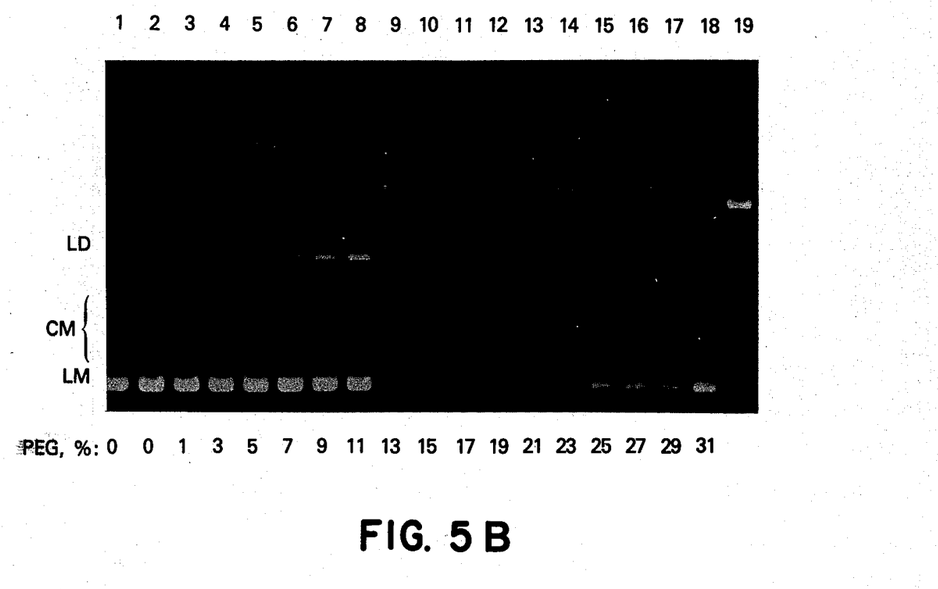

FIG. 5. Effects of PEG 6000 concentration on blunt-end ligation of DNA by T4 DNA ligase or on sedimentability of the DNA. Ligase assay mixtures with the PvuII nuclease-digested DNA substrate were as in Methods but doubled in volume to 60 μl, and contained the indicated (w/v) concentrations of PEG 6000. T4 DNA ligase (1.25 units) was present in lanes 2-18. A mixture of HindIII endonuclease-digested λ DNA and λ DNA was added for lane 19; sizes in kilobase pairs are indicated in the right margin. After incubation, 30 μl aliquots were processed as in Methods for the 0.8% agarose gel shown in (A), while the remainder of each of the mixtures was centrifuged for 5 min. at room temperature at 15,000×g and the supernatant fluids were removed and then similarly processed for the gel shown in (B). LM, linear monomer; CM, circular monomers; LD, linear dimer.

Figure 6A:
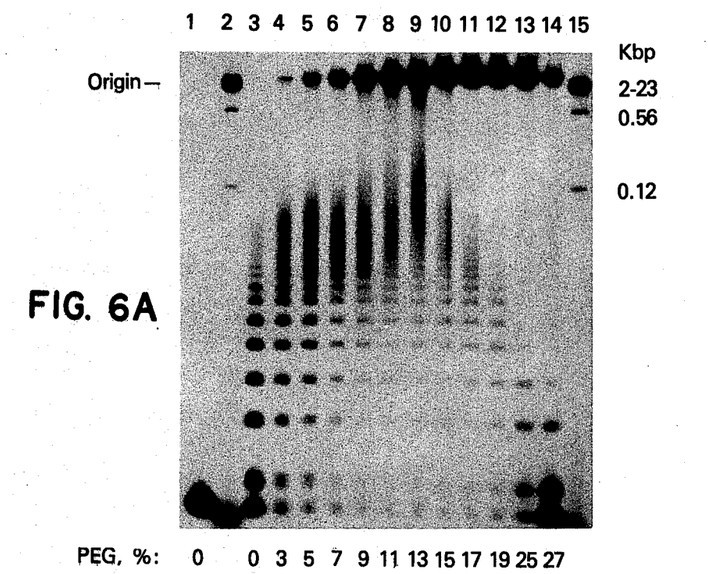
FIG. 6 is a gel electrophoretic pattern illustrating the effect of PEG 6000 concentration on the blunt-end ligation of deoxyribooligonucleotide by T4 DNA ligase.
Figure 6B:
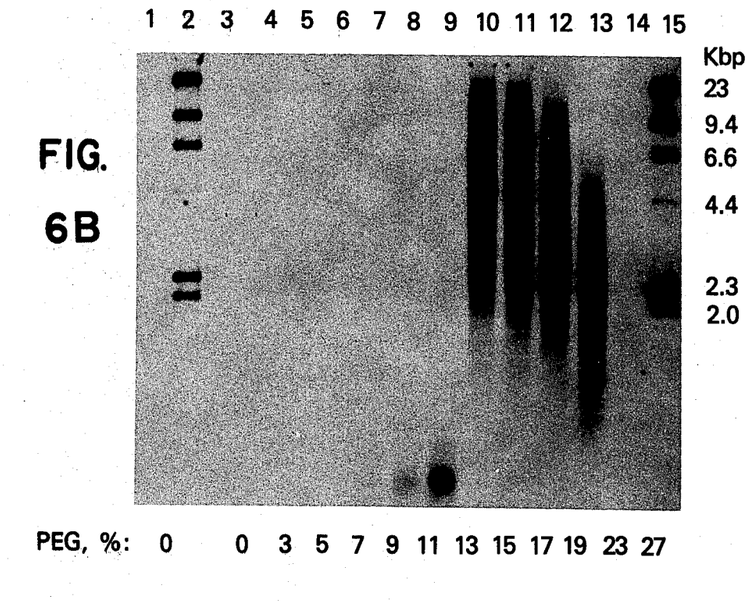

FIG. 6. Effect of PEG 6000 concentration on the blunt-end ligation of d(CGGGATCCCG) by T4 DNA ligase. Ligase assay mixtures (20 µl) as in Methods contained 5'$^{32}$P-d(CGGGATCCCG) in place of the DNA substrate and PEG 6000 at the (w/v) concentrations indicated. T4 DNA ligase (0.6 unit) was added for lanes 3–14. A $^{32}$P-labeled HindIII nuclease digest of λ DNA was present in lanes 2 and 15; sizes of fragments in kilobase pairs are indicated in the right margins. After incubation, samples were taken for a 12% acrylamide-7M urea gel (A) and a 0.8% agarose gel (B) as in Methods.

Figure 7A:
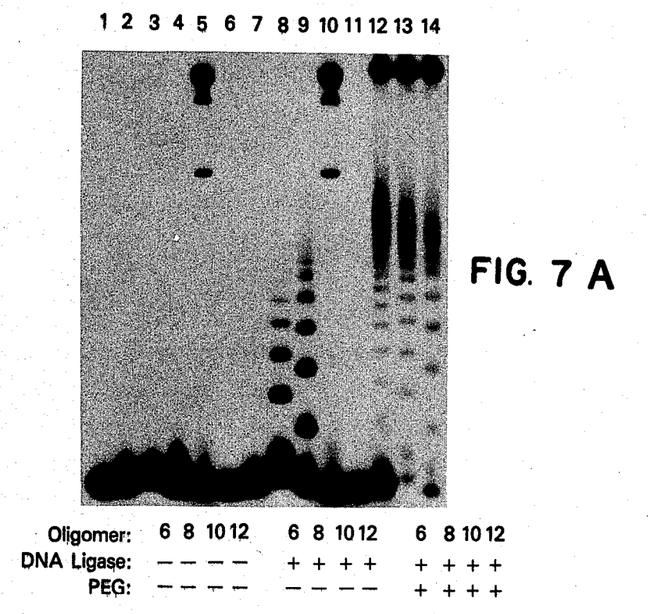
FIG. 7 is a gel electrophoretic pattern illustrating an effect similar to that of FIG. 6.
Figure 7B:
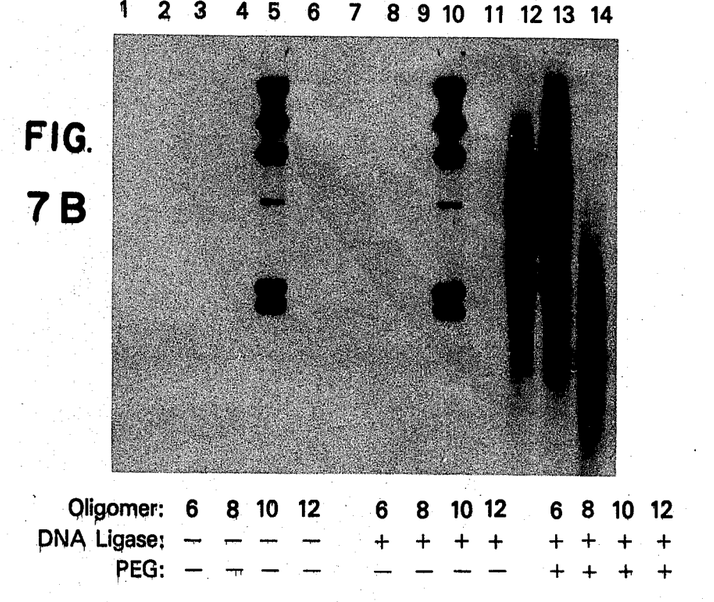

FIG. 7. Effect of PEG 6000 on the blunt-end ligation of self-complementary deoxyribooligonucleotides of 6, 8, 10, or 12 nucleotides in length. Ligase assay mixtures (20 µl) as in Methods contained 5'-$^{32}$P-deoxyriboolig­omers as follows in place of the DNA substrate: Lanes 1, 6, 11-d(CCCGGG); lanes 2, 7, 12-d(CCAGCTGG); lanes 3, 8, 13-d(CGGGATCCCG); lanes 4, 9 14 d(CCGGAATTCCGG). T4 DNA ligase (0.6 unit) was added in lanes 6-9 and 11-14. PEG 6000 (15% w/v) was present in lanes 11-14. A $^{32}$P-labeled HindIII nuclease digest of DNA was present in lanes 5 and 10. After incubation, samples were taken for a 12% acrylamide-7M urea gel (A) and a 0.8% agarose gel (B) as in Methods.

Figure 8:
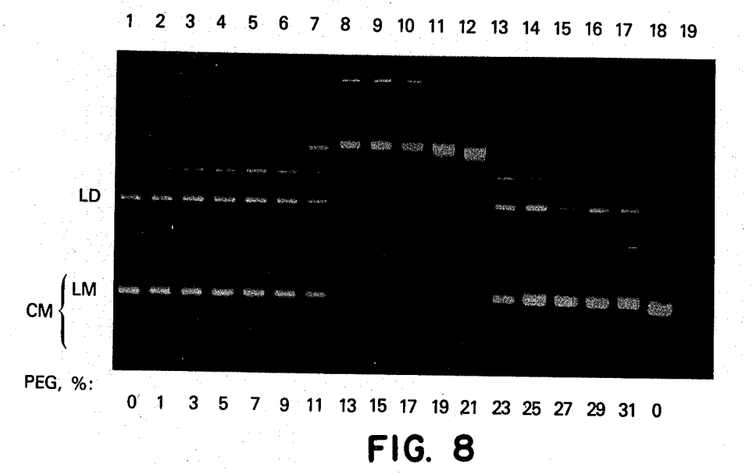
FIG. 8 is a gel electrophoretic pattern illustrating the effect of PEG 6000 concentration on cohesive-end ligation of DNA by T4 DNA ligase.

FIG. 8. Effect of PEG 6000 concentration on the cohesive-end ligation of DNA by T4 DNA ligase. Ligase assay mixtures were as in Methods, and contained BamHI nuclease-digested pBR322 DNA. PEG 6000 was added at the (w/v) concentrations indicated. T4 DNA ligase (0.28 unit) was in lanes 1-17. A mixture of HindIII-nuclease-digested λ DNA and λ DNA was present in lane 19. Gel, 0.8% agarose. LM, linear monomer; CM, circular monomers; LD, linear dimer.

Figure 9:
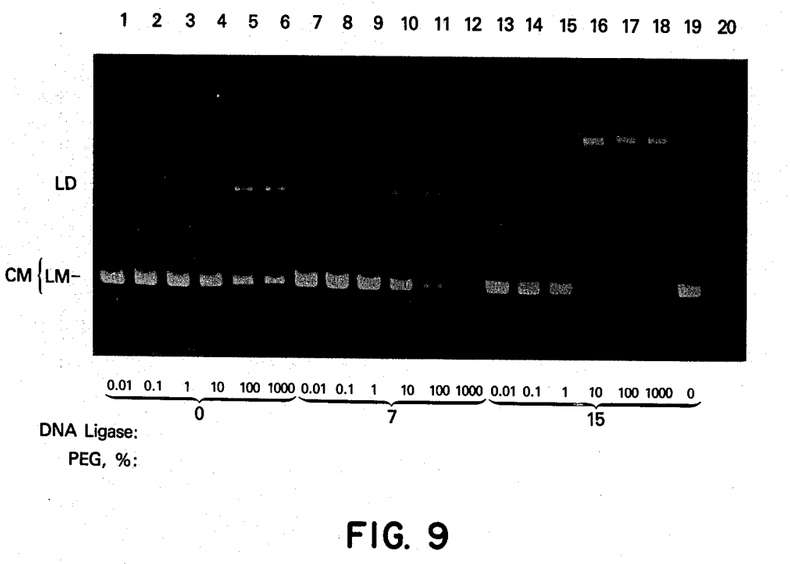
FIG. 9 is a gel electrophoretic pattern illustrating the effect of PEG 6000 concentration on cohesive-end ligation of DNA as a function of ligase concentration.

FIG. 9. Effect of PEG 6000 on the cohesive-end ligation of DNA as a function of T4 DNA ligase concentration. Ligase assay mixtures were as in Methods, and contained 0.3 µg of BamHI nuclease-digested pBR322 DNA. The concentrations of PEG 6000 (w/v) and T4 DNA ligase were as indicated with a relative amount of T4 DNA ligase of $1 = 2.5 \times 10^{-3}$ units/assay. A mixture of HindIII nuclease-digested λ DNA and of λ DNA was present in lane 20. Gel, 0.8% agarose. LM, linear monomer; CM, circular monomers; LD, linear dimer.

DETAILED DESCRIPTION OF THE INVENTION

Figure 1A:
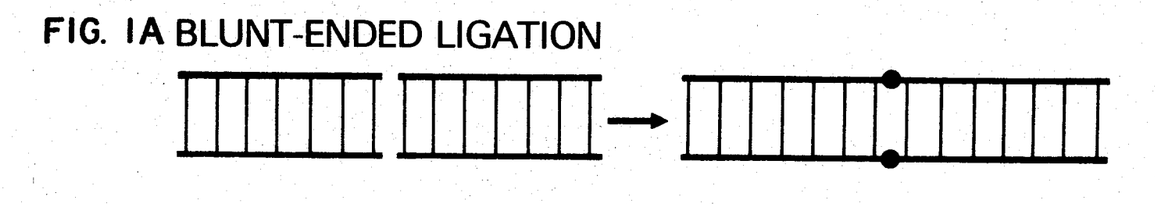
FIG. 1 is a schematic illustration of the ligation of different strand-breaks in double-stranded DNA.
Figure 1B:
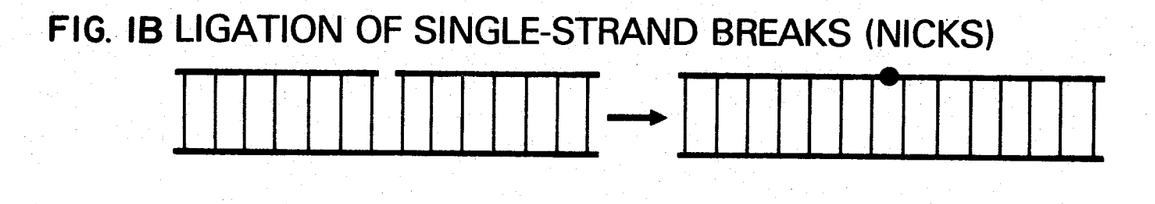
Figure 1C:
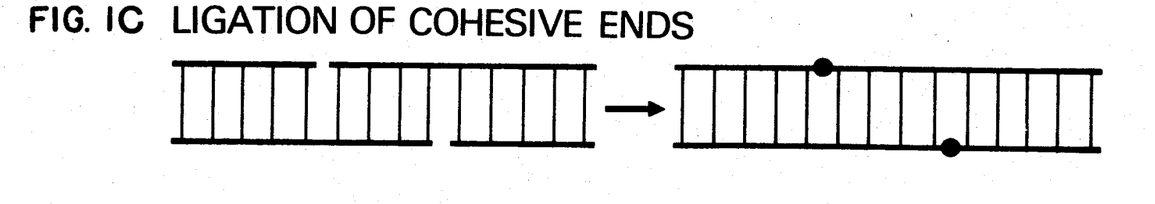

Ligation of duplex DNA is critical to the production of hybrid plasmids. Typically, a selected DNA substrate is digested with a restriction endonuclease or other DNA cleavage enzyme to provide DNA fragments having flush or blunt-ended termini (FIG. 1(a)) or cohesive termini (FIG. 1(c)); the fragments to be ligated are modified as necessary to provide compatible ligatable termini for covalent bonding (see, e.g., Cohen et al, U.S. Pat. No. 4,237,224). The ligation of duplex DNA fragments with either blunt or cohesive ends is typically presently accomplished by enzymatic ligation in dilute solution with T4 DNA ligase, a ligase derived from E. coli infected with T4 bacteriophage (see, e.g., Sgaramella, et al, J. Mol. Biol. 72:427-444, 1972, and Sgaramella, PNAS 69:3389, 1972). The cohesive-end ligation of duplex DNA fragments is also accomplished by other known DNA ligases; however, these ligases have no appreciable blunt-end ligation activity in conventional ligation media, although it is assumed that a low level of activity is present.

In accordance with the present invention, DNA ligase activity is accelerated by the presence of macromolecular species, or mixtures of macromolecular species, in conventional DNA ligation media. The increased enzyme activity is primarily reflected in an increased ligation rate for a given system, which may be accompanied by an ultimate increase in ligation product. The invention broadly contemplates the use of volume excluding polymers to increase the ligation activity of enzymes comprising DNA ligases on a complete spectrum of both blunt-end and cohesive-end linear duplex DNA substrates, with significant increases in enzyme activity for all ligation systems within the scope of the invention. In particular, blunt-end ligation of DNA fragments by T4 ligase is strongly accelerated by the presence of macromolecular species in conventional DNA ligation media. Further, while in dilute ligation media the T4 ligase product is primarily closed circular DNA, in the presence of macromolecular crowding the reaction equilibrium is changed to provide a product in which linear oligomers predominate. Ligation of blunt-ended, double-stranded self-complementary pairs of deoxyribooligonucleaotides as short as 8 base pairs to each other or to DNA fragments as linkers, is similarly accelerated. Ligation of DNA fragments or duplex deoxyribooligonucleotides having cohesive termini by T4 ligase is stimulated to a lesser extent while sealing of nicks in the DNA molecule (FIG. 1(b)) is relatively unaffected. It has also been found that rat liver nuclear DNA ligase and E. coli DNA ligase catalyze blunt-end ligation under conditions of macromolecular crowding according to the invention, in contrast to the lack of blunt-end ligation activity exhibited in conventional dilute ligation media.

In carrying out the inventive process, sufficient macromolecular material is added to a conventional DNA ligation system to obtain the desired increase in enzymatic activity and/or the desired product characteristics. For a given DNA ligase/DNA substrate system, the activity of the enzyme and characteristics of the ligation products will be generally dependent upon the macromolecular species employed, its molecular weight, and the volume fraction of the ligation medium occupied by the macromolecular species.

Suitable macromolecular materials broadly comprise biocompatible natural or synthetic polymers having an average molecular weight of from about 1500 to several million, which do not specifically interact with the DNA substrate, the DNA ligase employed, or the product. Such polymers are known in the art as "volume-excluders", as their primary function is to occupy volume in the in vitro reaction medium and provide a highly concentrated environment for biochemical reactions, approximating in vivo conditions. The volume-excluding polymers must of course be sufficiently soluble to provide the required concentration in the ligation medium, and preferably do not substantially hinder subsequent manipulative steps.

Suitable exemplary polymers include commercially available polyethylene glycol (PEG) polymers having an average molecular weight greater than about 2000, FICOLL polymers such as those having an average molecular weight of about 70,000, bovine plasma albumin, and glycogen. PEG polymers of higher molecular weights, especially, PEG 1450, PEG 3350, PEG 6000

(also sold as PEG 8000), and PEG 20,000, having average molecular weights of about 1450, 3000–3700, 6000–7500, and 15,000–20,000, respectively, are particularly effective in increasing enzyme activity. PEG 6000 and PEG 8000 are especially useful in obtaining maximum production of linear DNA aggregates, of relatively high molecular weight. PEG polymers also have preparative advantages in that separation of volume excluder from ligation product is facilitated with this species—further, its presence has proved innocuous in many applications.

The concentration of the volume-excluding polymers in the ligation medium necessary for optimal enzyme activity in a given system will usually fall within a range of about 5% w/v to about 45% w/v, depending upon the type of polymer and its molecular weight. In general, it is expected that a given type of polymer of higher molecular weight need be present in lower concentration than the same type of polymer of lower molecular weight to achieve the same effect on enzyme activity.

It is contemplated that for a selected conventional DNA ligase/DNA substrate system, specific polymers of a given molecular weight within the scope of the invention will each provide an optimum, reproducible increase in enzyme activity within a characteristic range of concentrations. This range will vary somewhat according to the specific ligation conditions employed, including the type of ligase, the type of DNA substrate, the salt concentration of the medium, the pH, and other conventional variables. However, very limited experimentation will be necessary to determine the optimum concentration range for a selected macromolecular species in a given system, by protocols for assessing enzyme activity well-known to those in the art. For example, a conventional in vitro ligation medium may typically comprise an aqueous solution (pH 6–8) at a temperature of about 5° C. to 40° C., with a concentration of DNA substrate of from about 1 to 100 µg/ml and of $T_4$ ligase of from about 1 to 100 u/ml; the ligation medium generally also includes $Mg^{++}$ in concentrations of about 3–10 mM. An exemplary ligation solution of this type is divided into several portions, to each of which is added a selected polymer of given molecular weight in varying amounts; samples are taken at appropriate intervals (usually ½ to 1 hour), and the amount of product obtained at each interval determined. Alternatively, a constant amount of polymer may be employed, and the amount of ligase varied from portion to portion of the digestion solution; in this instance the amount of product obtained in each test portion is determined at the end of an arbitrary digestion period. The effect of conventional variables on enzyme activity in the presence of a particular macromolecular species is similarly determined; the concentration of $Mg^{++}$, in particular, may be found to have a significant effect on the concentration of volume excluder necessary to optimize enzyme activity. A minimum concentration of $Mg^{++}$ unbound by ATP, may be required.

The process of the present invention is useful in controlling product distribution of enzymatic ligations of DNA, especially to maximize production of linear aggregates. As previously noted, T4 ligase DNA product in dilute medium is predominantly circular, primarily monomeric circles, with some dimeric circles present. In macromolecularly crowded media, however, the major T4 ligase product typically comprises linear oligomers, many of which are approximately equivalent to a decamer. The linear oligomers described herein comprise linear aggregates of two or more DNA substrate units, covalently bonded by ligation according to the process of the invention. Individual substrate units, including DNA fragments and oligonucleotides, are referred to in the art as "monomers" or "molecules", and ligation of two or more of these units is termed "intermolecular ligation", in contrast to cyclization of a single unit, which is "intramolecular ligation". Rat liver nuclear DNA ligase and E. coli DNA ligase produce linear oligomers, typically dimers to pentamers for E. coli DNA ligase, and much larger for rat liver DNA ligase, with the largest of the rat liver DNA digestion products being about a decamer in size. The linear products can be cyclized, if desired, by standard techniques such as employed for recircularizing plasmids after introduction of foreign DNA. Product distribution is also dependent upon concentration of volume-excluding polymer in a specific system, and can easily be determined by standard gel electrophoresis procedures, if desired, in conjunction with product digestion by λ DNA exonuclease, to which the circular species are resistant and the linear species are sensitive. Although maximum product size and enzyme activity are both dependent on polymer concentration, the optimum concentration ranges of macromolecular species to achieve these results are not necessarily coincident, and should be evaluated for each system employing the appropriate guidelines set forth supra.

The routine DNA ligase substrates employed in the exemplifications of the invention comprise linear, double-stranded DNA monomers obtained by the conventional action of Pvu II or Xmn I restriction endonucleases on pBR322 plasmid DNA to provide flush-ended monomer or by the conventional action of Bam Hl restriction endonuclease on this DNA to provide cohesive-ended monomer having protruding 5'-termini with a complementary overlap of four bases. These exemplifications are, however, merely illustrative. Suitable ligase substrates within the scope of the invention include linear DNA duplexes, either natural or synthetic, which have compatible ligatable termini. The ligatable termini may be blunt-ended, having two fully base-paired termini, or be cohesive-ended, having complementary protruding nucleotide sequences. Duplexes useful in the practice of the invention include double stranded DNA molecules, double stranded DNA fragments produced by the action of any suitable restriction enzyme, or double-stranded duplexes prepared from complementary deoxyribooligonucleotides including self-complementary oligonucleotides such as the adaptor molecules described by Wu, et al in U.S. Pat. No. 4,321,365 (1982). Mixtures of DNA duplexes may be used as substrate: for example, a double-stranded duplex prepared from a pair of self-complementary synthetic oligo deoxyribonucleotides may be ligated to a cleaved cloning vehicle. The disclosure has made reference to three DNA ligases, namely those from rat liver nuclei and from uninfected or T4-infected E. coli. These three enzymes represent both eukaryotic and prokaryotic sources, and have been very thoroughly characterized. It is contemplated that a broad range of eukaryotic and prokaryotic DNA ligases will be useful in conjunction with the present invention, based on the similar properties of known DNA ligases and the postulation that volume exclusion phenomena are substrate-related and are probably expressed independently of the idiosyncrasies of individual enzymes within a group.

EXAMPLES

A. MATERIALS AND METHODS

Enzymes. Lambda exonuclease, Bam Hl nuclease, and XmnI restriction endonuclease were purchased from New England Biolabs. PvuII restriction endonuclease was a product of either New England Biolabs or Bethesda Research Laboratories and T4 DNA ligase was from Bethesda Research Laboratories. *E. coli* DNA ligase Fraction VII was a gift from Dr. M. Gellert. Rat liver DNA ligase Fraction IV (10) was purified as previously described.

DNA and DNA Digestions. pBR322 DNA was either a gift from Dr. M. Gellert or the product of Bethesda Research Laboratories. Lambda DNA was from New England Biolabs, while a HindIII digest of DNA was obtained from Bethesda Research Laboratories. Digestions of pBR322 DNA with PvuII, BamHl, or XmnI restriction nucleases were done under the conditions suggested by the suppliers; the digested DNA was isolated by phenolchloroform extraction and ethanol precipitation. *E. coli* DNA (P-L Biochemicals) was labeled with $^{32}$P at the 5'-phosphate termini of nicks introduced by pancreatic DNase I as previously described for calf thymus DNA (Zimmerman, et al, J. Biol. Chem. 250: 149-155, 1975).

Solutions of Volume Excluders. Stock solutions of 40% w/v PEG 6000 (Eastman Kodak), 70% w/v Ficoll 70 (Pharmacia), or 50% w/v crystallized bovine plasma albumin (Miles) were made in deionized water. The albumin solution was adjusted to pH 7.6 with 0.08 volume of 1M NaOH. PEG 200, a liquid, was purchased from Baker Chemical. Other stock solutions of macromolecules were at 40-70% w/v in deionized water. Glycogen was extracted from rabbit liver with an equal volume of 10% trichloroacetic acid, repeatedly precipitated from neutralized aqueous solution with an equal volume of 95% ethanol, washed with diethyl ether, and air dried.

High concentrations of the polymer solutions have caused surprisingly few experimental difficulties beyond those in accurately making and pipetting the sometimes very viscous solutions. The polymer stock solutions were stored frozen or were refrigerated; aliquots were warmed to room temperature before distribution into reaction mixtures in order to decrease their viscosity and improve the reproducibility of volume measurements. Ligation mixtures were routinely formed at 0°; however, mixtures with Ficoll 70 were prepared at room temperature because of the high viscosity of concentrated cold solutions of this material. High levels of PEG 6000 or Ficoll 70 in samples for gel electrophoresis made no detectable changes in the migration of DNA standards while albumin solutions caused only relatively minor effects if diluted to <16% before electrophoresis. The ligases and several restriction endonucleases were relatively stable and active in such solutions. PEG 6000 has an advantage in that it can be easily removed from DNA solutions by extraction with chloroform.

$^{32}$P-labeling of Oligomers or DNA. Deoxyribooligonucleotides lacking terminal 5'-phosphate groups were purchased as follows: d(CCGGAATTCCGG), d(CGGGATCCCG), and d(CCAGCTGG) from New England Biolabs; d(CCCGGG), d(AGCT), and d(CCGG) from P-L Biochemicals. These oligomers were $^{32}$-P-labeled using polynucleotide kinase (P-L Biochemiclas) in successive incubations with $\gamma$-$^{32}$P-ATP (New England Nuclear, 2900 Ci/mmol) and with unlabeled ATP. HindIII nuclease-digested λ DNA and PvuII nuclease-digested pBR322 DNA were dephosphorylated with *E. coli* alkaline phosphatase (Millipore) prior to labeling with $^{32}$P.

Gels. Electrophoresis in 0.8% agarose gels was as described by Gellert et al. (Proc. Natl. Acad. Sci. USA 73: 3872-2876, 1976), using a horizontal slab gel apparatus. Gels with unlabeled samples were stained with ethidium bromide and photographed. Gels containing $^{32}$P samples were dried under vacuum while supported by absorbent paper (Bio-Rad Labs) before autoradiography at 5° with XAR-5 film in X-Omatic cassettes (Eastman Kodak).

Acrylamide gels of 1.5 mm thickness containing 11.5% acrylamide—0.4% bis-acrylamide—7M urea in 0.05M Tris—0.05M boric acid—1.4 mM EDTA buffer were elctrophoresed in a vertical slab gel apparatus (Model SE 400, Hoefer Scientific) and evaluated by autoradiography as above.

DNA Ligase Assays. DNA ligases were routinely assayed in mixtures (10-40 μl) containing 50 mM Tris. HCl buffer, pH 7.8, 5 mM MgCl$_2$, 10 mM β-mercaptoethanol, 0.3 μg PvuII or Bgm Hl endonuclease-digested pBR322 DNA or 4 μM (on a nucleotide basis) 5'-$^{32}$P-deoxyribooligo-nucleotides, and 0.3 volume of ligase dilution (in 10 mM β-mercaptoethanol—20 mM Tris. HCl buffer, pH 7.8-25% w/v glycerol—10 μg/ml crystallized bovine plasma albumin). In addition, the mixtures contained either 0.5 mM ATP in assays of the rat liver or T4 DNA ligases, or 27 μM NAD+ and 1 mM NH$_4$Cl in assays of the *E. coli* ligase. After incubation at 20° C. for the times indicated, 0.25 volume of Mixture A (20 mM EDTA—23% glycerol—0.23 mg/ml bromphenol blue—4.5% sodium dodecylsulphate) was added and the samples were applied to a horizontal slab gel. The gel composition, electrophoresis and photography were as described by Gellert et al., supra. For labelled reaction mixtures, separate aliquots were usually removed for agarose gels (diluted with 0.25 volume of Mixture A) or for acrylamide gels (diluted with 1.3 volumes of 0.09N NaOH—1.8 mM EDTA—0.14 mg/ml bromphenol blue-0.4 mg/ml Orange G—8M urea; samples heated 1 min at 90°-100° and quenched at 0° before electrophoresis).

Assay for Sedimentability of DNA. Mixtures as described for DNA ligase assays were centrifuged for 5 min at room temperature at 15,000×g (Eppendorf). The supernatant fluids were mixed with 0.25 volume of Mixture A prior to agarose gel electrophoresis.

B. RESULTS

1. Blunt-End Ligation with various DNA Ligases in Concentration Polymer Solutions. Purified preparations of the DNA ligases from rat liver nuclei or from *E. coli* are inactive in assays for blunt-ended DNA joining under the conventional dilute-solution conditions used for assaying this type of reaction with the T4 DNA ligase (FIG. 2, lanes 1 or 7 vs. lane 13). Assays for blunt-end ligation by the rat liver or *E. coli* enzymes under related conditions in which the pH, ionic strength, or temperature were varied were also negative, as were assays under a variety of conditions described in the literature which include additions of T4 RNA ligase, spermidine, or hexamine cobalt chloride. (Pheiffer and Zimmerman, unpublished data). The situation changes dramatically in crowded solutions. In the presence of high concentrations of a number of macromolecular solutes, both the rat liver and *E. coli* DNA ligases exhibit high levels of blunt-end ligation; the activity of the T4 DNA ligase is stimulated by about a thousand-fold (FIG. 3) and the product distribution is modified under these conditions. The effect of changes in PEG 6000 concentration on the ligation of linear blunt-ended pBR322 is shown in FIG. 2 for all three ligases: The *E. coli* ligase (lanes 1–6) and the rat liver ligase (lanes 7–12) both form a series of products as the PEG 6000 concentration is raised. The nature of these products is discussed infra; they are related to the products formed by the T4 DNA ligase (lanes 13–18, FIG. 2).

The effect is not specific with regard to the type of macromolecule. A generally similar response to that elicited by PEG 6000 was obtained at high concentrations of the branched polysacchararide, Ficoll 70 (FIG. 4: lanes 2–5 for *E. coli* ligase; lanes 7–10 for rat liver ligase) or a protein, bovine serum albumin (FIG. 4: lanes 12, 15 and 18 for *E. coli ligase;* lanes 13, 16 and 19 for rat liver ligase). In contrast to the effect of Ficoll 70, its monomer, sucrose, did not allow blunt-end ligation even at very high concentrations when it replaced the polymer in this assay system (tested at 14, 28, 42, 56, or 70% w/v sucrose; data not shown). Similarly, polyethylene glycol of lower average molecular weight, PEG 200, did not support blunt-end ligation by the rat liver or *E. coli* ligases (tested at 11, 19, 27, 43, 58 or 82% w/v PEG 200; data not shown).

Concentrated solutions (12 or 24% w/v) of rabbit liver glycogen were effective stimulators of blunt-end ligation by the T4 DNA ligase. The glycogen caused extensive smearing of the electrophoretic patterns so that samples for gels were incubated with an α-amylase (1–10 units of 4-fold crystallized *B. subtillis* α-amylase, Sigma) before electrophoresis (data not shown).

Small stimulations (up to ca. 3-fold) were obtained at high levels of dextrans (above 16% w/v dextran T-70 and above 6% w/v dextran T-500).

2. Blunt-End Ligation of DNA Fragments with T4 Ligase in PEG 6000 Solutions a. Increase in ligation rate due to PEG 6000. The rate of blunt-end ligation under our standard assay conditions is approximately proportional to enzyme concentration and to time except at very low or very high extremes of reaction. Based on assays between these limits, stimulation of the rate of T4 DNA ligase by 15% w/v PEG 6000 is well over a thousand-fold (FIG. 3). At 7% w/v PEG 6000, a much smaller stimulation (up to 5-fold) is obtained which may prove useful in augmenting circle formation.

b. Two-phase behavior. The DNA present in ligase assay mixtures containing relatively high concentrations (15% w/v) of PEG 6000 becomes readily sedimentable. This change in the DNA indicates the presence of two phases, although no visually obvious change has been noted. The concentration of PEG 6000 at which the stimulation of ligation occurs is correlated with that at which the DNA becomes sedimentable (FIG. 5A vs. FIG. 5B). The transition in both parameters occurs over a narrow range of PEG 6000 concentrations (<1% w/v concentration difference), this sharpness again being consistent with a phase transition. If desired, the DNA can be made non-sedimentable simply by diluting the PEG 6000 to 5% w/v with 0.01M Tris HCl, pH 8—0.1 mM EDTA after completion of the ligation reaction. However, the sedimentability of the DNA can be turned to advantage as a means of reisolating the DNA in a concentrated form largely freed of PEG 6000; the mixtures are simply centrifuged at 15,000×g for 5 min. at room temperature or at 5° and the supernatant fluids removed. The DNA is readily redispersed in solvents such as 0.01M Tris HCl, pH 8—0.1 mM EDTA by occasional mixing over a 5 min. period. Another alternative is to extract the PEG with CHCl₃; a single extraction with 3 volumes of CHCl₃ at room temperature removed 95% of the PEG 6000 (estimated gravimetrically, data not shown). The PEG in uncharged, so that it should be separable from DNA and related materials by electrophoresis. The possibility of acquired charge on the PEG due to the adsorption of charged detergents such as sodium dodecylsulfate may need to be considered. For many purposes, the continued presence of the PEG seems to be quite innocuous.

The effect of albumin or Ficoll solutions differs from that of PEG 6000 in the lack of sedimentability of the DNA in solutions of the former materials over the entire ranges of concentrations tested (data not shown).

3. Effects of PEG of Varying Molecular Weight on Blunt-End Ligation by T4 DNA Ligase Larger polyethylene glycols, PEG 3350, PEG 6000 and PEG 20,000 (average molecular weights 3000–3700, 6000–7500 and 15,000–20,000, respectively) all gave similar large stimulations in rates of blunt-end ligation by the T4 DNA ligase. The major difference between samples of PEG in this size range is the PEG concentration at which the effect takes place. The influence of PEG 6000 concentration is shown in detail in FIG. 5A. In the range between 13% and 23% w/v PEG 6000, the rate of ligation is strikingly increased (see below). Beginning also at about 13% w/v PEG 6000 and continuing through the highest concentration tested, and bulk of the DNA becomes readily sedimentable (FIG. 5B). (Similar ligase stimulations occurred in 15% to 21% w/v PEG 3350 and in 12.5% to at least 14% w/v PEG 20,000; data not shown.) In contrast, polyethylene glycols of short chain length gave little stimulation. For example, PEG 200 or PEG 400 (average molecular weights 190–210 or 380–420, respectively) gave only 2- to 3-fold increases in the rate of ligation at PEG concentrations above ca. 29% or 36% w/v, respectively. (The stimulation by PEG 400 was accompanied by conversion of the DNA to a readily sedimentable form; PEG 200 was not similarly tested.)

4. Blunt-End Ligation of Deoxyribooligonucleotides with T4 Ligase

T4 DNA ligase can join blunt-ended duplex deoxyribooligonucleotides as short as 7 base pairs or 8 base pairs in length. Ligation of such substrates was stimulated by high concentrations of polymers in a manner generally similar to the stimulation of joining of large pieces of duplex DNA described above. In the following experiments, the 5'-phosphate termini of the oligomers were labeled with $^{32}P$. Reaction mixtures were evaluated either by direct autoradiography of 12% acrylamide-7M urea gels (to determine single-strand chain length of the shorter products) or by autoradiography of the usual 0.8% agarose gels after drying of the gel. Although the smaller products and the substrate were lost from such dried agarose gels, those oligonucleotides were recovered on the acrylamide gels.

a. Effect of PEG 6000 or Ficoll 70 concentration on blunt-end ligation of d(CGGGATCCCG). As the concentration of PEG 6000 was raised, the amount and size of the products of ligation of the self-complementary deoxyribodecanucleotide, d(CGGGATCCCG), increased (FIG. 6, A and B). In 15–19% w/v PEG 6000, a very large increase in size occurred, with the average size of the product being about 4000 base pairs (FIG. 6B). Comparison of products formed at different ligase concentrations and times indicated that the stimulation of the rate of decamer sealing by 15% w/v PEG 6000 was between 10–50-fold. High concentrations of Ficoll 70 also stimulated ligation of the decamer, although the sizes of the products were generally at least several-fold smaller than with PEG 6000.

b. Comparison of the PEG 6000 effect on blunt-end ligation of several deoxyribooligonucleotides of different chain lengths. Self-complementary deoxyribooligonucleotides of various base-sequence with chain lengths of 4 (d(CCGG) or d(AGCT)), 6 (d(CCCGGG)), 8 (d(CCAGCTGG)), 10 (d(CGGGATCCCG)), or 12 (d(CCGGAATTCCGG)) bases were tested for blunt-end ligation by T4 DNA ligase at either 0 or 15% w/v PEG 6000. Neither of the tetramers nor the hexamer were ligated in the presence or absence of PEG 6000 at the usual assay temperature (20°) or at 4°; the hexamer was not ligated in long incubations at 0° when 1 mM spermidine or 0.1M or 0.3M NaCl was present with or without the 15% w/v PEG 6000 (data not shown). The 8-, 10-, or 12-mers, which were all ligated to relatively low extents in the absence of PEG 6000 by the level of T4 ligase used, showed dramatic increases in the amount and chain length of product made in the presence of 15% w/v PEG 6000 (FIG. 7, A and B). Ligation in 15% w/v PEG 6000 of either the 8-mer or 12-mer, was slightly slower at 0° than at 20° (data not shown).

c. Blunt-end ligation of d(CGGGATCCCG) to DNA. It has proven useful to be able to ligate a "linker", i.e. a small self-complementary deoxyribooligonucleotide containing a specific restriction sequence, to the ends of DNA. The effect of PEG 6000 on this type of reaction was tested, using mixtures of equal weights of the usual unlabeled blunt-ended linear pBR322 DNA substrate and of $5'-^{32}P$ d(CGGGATCCCG). When 15% w/v PEG 6000 was present, the self-ligation reaction of the DNA proceeded as if it was occurring in the absence of decamer, but in addition there was significant labeling of large DNA aggregates by joining to the $^{32}P$-decamer.

5. Cohesive-End Ligation of DNA in PEG 6000 Solutions

Sealing of cohesive termini is stimulated in concentrated PEG 6000 solutions in a manner generally similar to that for the sealing of blunt-ended termini. The DNA substrate we have used for cohesive ligation is pBR322 DNA cut at a single site by restriction endonuclease BamHI, generating protruding 5'-termini with a complementary overlap of four bases. The influence of PEG 6000 concentration on the sealing of this substrate is shown in FIG. 8, which may be compared with the identical experiment carried out with blunt-ended DNA shown in FIG. 5A. The rates of sealing in the absence of PEG 6000 or at low levels of this polymer are much higher for the cohesive-ended termini of FIG. 8 compared to those on the blunt-ended termini of FIG. 5A—in accord with the general experience that cohesive termini are more readily sealed than are blunt-ended termini. Beyond this difference, there is an additional stimulation of perhaps two-fold by 7% w/v PEG 6000 and a ca. 10- to 100-fold stimulation by 15% w/v PEG 6000 (FIG. 9; this figure may be compared to the identical experiment with blunt-ended DNA shown in FIG. 3).

6. Identification of the Products of Blunt-End Ligation

The routine DNA substrate for the blunt-end ligation assays is the linear flush-ended duplex DNA molecule formed by single-site cleavage of pBR322 DNA ($2.7 \times 10^6$ daltons) with PvuII restriction endonuclease. In principle, such a substrate can undergo either intramolecular ligation to form a circular product or intermolecular joining to yield linear oligomers-which may then also be cyclized. The criteria used to identify circular ligation products were their mobilities on gels relative to standard materials, their resistance to λ exonuclease, and the presence of the characteristic distribution of closed circular DNA topoisomers.

T4 DNA ligase forms relatively large amounts of monomer circles and smaller amounts of dimer cicles if assayed at low concentrations of background macromolecules (e.g. lanes 13–15, FIG. 2; several topoisomers of monomer circles are visible above the lowest band (linear monomer substrate). In contrast, circular monomers or dimers are not major products of either the E. coli or rat liver enzymes under any of the conditions tested, based on their absence on ethidium-stained gels. (More sensitive assay by autoradiography indicated that small quantities of monomer circles could be formed by the rat liver enzyme in 6–11% PEG 6000). Lambda exonuclease treatment of E. coli or rat liver ligase products confirmed the relative absence of circular molecules.

The size distribution of linear oligomers made by the ligases in crowded solutions ranged from dimer through pentamer for the E. coli ligase to considerably larger oligomers for the other enzymes. For the rat liver ligase, the largest linear products were similar in gel mobility to λ DNA ($33 \times 10^6$ daltons), comparable to a decamer in size, whereas a significant proportion of the linear products of the T4 ligase were larger than λ DNA based on migration in 0.5% agarose gels (data not shown).

a. Identification of DNA products of blunt-end ligation in PEG 6000. At ≧15% PEG 6000, the product formed by T4 DNA ligase contained no detectable circular monomers or circular dimers (FIG. 5A). The bulk of the product made in 15% w/v PEG 6000 is sensitive to λ exonuclease under conditions where closed circular standards are resistant and linear standards are degraded (data not shown). A significant portion of the linear oligomers made in 13% w/v PEG 6000 is larger than λ DNA ($33 \times 10^6$ daltons), corresponding to a ca. 10-fold increase in size, based on migration in 0.5% agarose gels (data not shown). A fraction of the DNA product formed at 13–21% w/v PEG 6000 does not enter 0.5 or 0.8% agarose gels. The resistance of this material to digestion by λ exonuclease and its behavior on gels is suggestive of very high molecular weight circular DNA molecules. This fraction as well as the linear aggregates which enter the gel are all products of blunt-end ligation at the PvuII site, as was previously demonstrated by completely recutting them to linear monomers with PvuII.

b. Identification of products of blunt-end ligation of d(CGGGATCCCG) in PEG 6000. The products formed by T4 DNA ligase from the decamer in 15% w/v PEG 6000 were tested for sensitivity to λ exonuclease essentially as described above for the corresponding experiment with the DNA substrate. At least 90% of the radioactivity in the products as assessed on either agarose or acrylamide gels was converted to mononucleotides by amounts of λ exonuclease which totally digested linear DNA standards but which did not degrade circular DNA standards when the unlabeled standards were added to the $^{32}$P-reaction mixtures at the stage of exonuclease digestion (data not shown). We therefore conclude that the ligation products of the decamer behave as linear rather than as circular molecules.

A number of aspects of the blunt-end ligation of a self-complementary octamer, d(TAGTACTA), by T4 DNA ligase in the absence of background polymers have been previously studied. In the products formed in the absence of PEG or at low PEG levels, there is a suggestion of the reported intermediates (e.g., lanes 3–6 of FIG. 6A), but at the higher PEG 6000 concentrations where significant stimulation occurs, there is no indication of intermediates (double bands) (e.g., lanes 10–12 of FIG. 6A).

7. Reaction Products Are Formed by Nonspecific Blunt-Ended Joining

Several lines of evidence indicate that the ligation of the PvuII digest of pBR322 described above is a blunt-ended DNA joining as opposed to sealing of cohesive ends (FIG. 1). First, the enzymes to which the DNA substrate is exposed are unlikely to generate significant amounts of termini other than the expected flush-ended DNA termini. The routine DNA substrate is a linear monomer length duplex produced by the action of restriction endonuclease PvuII. This enzyme is known to make a flush-ended cut at a unique site on pBR322. The preparations of PvuII used were essentially free of non-specific endonuclease activity under the conditions employed, as judged by lack of activity upon a deletion mutant of pBR322 which lacks the PvuII recognition sequence (kindly provided by Dr. K. Mizuuchi). The ligase preparations all are free of detectable 5'-exonuclease based on a lack of release of radioactivity from terminally labeled DNA substrate. Further, the PvuII nuclease readily converted the ligation products back to linear monomers.

8. Recommended Best Mode Reaction Conditions for Linear or Circular DNA Products Maximal production of linear aggregates by blunt-end ligation of DNA or small deoxyoligomers or by cohesive-end ligation of DNA was obtained in mixtures containing 15% w/v PEG 6000 or PEG 8000; 50 mM Tris HCl, pH 7.8; 0.5 mM ATP; 10 mM β-mercaptoethanol; 5 mM MgCl$_2$; T4 DNA ligase; DNA or deoxyribooligomer. Enzyme dilutions were made in 10 mM β-mercaptoethanol; 20 mM Tris HCl, pH 7.8; 25% v/v glycerol; 10 μg/ml bovine plasma albumin. Reaction mixtures were prepared at 0°. All components except the PEG and ligase were first added and mixed. An appropriate volume of a 40% w/v stock solution of PEG 6000 (or PEG 8000) was then added and thoroughly mixed, followed by ≦0.3 volume of ligase dilution. Incubation was at 20° for 0.5 to 16 hours. (PEG 8000 purchased from J. T. Baker or Sigma gave a pattern of stimulation indistinguishable from PEG 6000 purchased from Kodak; PEG 8000 purchased from Sigma is stated to be the same as the material previously sold as PEG 6000, reflecting improved analytical data.)

The extremes of the PEG 6000 concentration range within which the phase transition occurred over the course of many experiments were 11% to 13% w/v with one exception. In that case, involving labeled preparations of DNA, the transition occurred at a significantly lower PEG 6000 concentration. It is discussed more fully supra.

Conditions have not been found which greatly improve the yield of circular DNA products. A relatively small stimulation (up to 5-fold but generally 3-fold) is obtainable in mixtures similar to those described above for maximizing linear aggregates except that a final concentration of 7% w/v PEG 6000 is used.

9. Influence of Temperature on Blunt-End Ligation

The distribution of products of blunt-end ligation by all three enzymes was generally similar in incubations at either 20° or 37°. The amount of product was somewhat reduced for the rat liver enzyme at 37°; the opposite was true for the E. coli ligase. The effect of temperature of blunt-end ligation by the T4 DNA ligase was measured at either 7% or 15% w/v PEG 6000. The lower PEG 6000 concentration was chosen to test the effect of temperature on the yield of circular products, whereas the higher concentration of PEG 6000 allowed a test of the effect of temperature on production of linear DNA aggregates. Under both conditions, incubation at 20° yielded 1.5- to 2-fold more of the products characteristic of the given level of PEG 6000 than did incubation at 12° or 37°, and 3- to 4-fold more than at 0° or 42°.

10. Influence of the Concentrations of DNA, Mg$^{++}$ or ATP on Blunt-End Ligation in PEG 6000 Solution The DNA concentration routinely used here is 10 μg/ml. Varying the DNA level from 2–50 μg/ml made <2-fold difference in the rate of ligation.

Blunt-end DNA ligation by the E. coli and rat liver ligases in the presence of high levels of PEG 6000 was readily observed at 60-fold lower DNA concentration (autoradiographic assay; data not shown).

The general effect of PEG 6000 concentration on blunt-end ligation at very low DNA concentration (0.5 μg/ml) was similar to that described above for higher DNA concentrations. Several experiments with terminally labeled DNA indicated a potential source of variation in the pattern of PEG 6000 stimulation. The labeled DNA substrate was PvuII nuclease-digested pBR322 DNA that had been dephosphorylated with E. coli alkaline phosphatase and rephosphorylated with polynucleotide kinase and γ-$^{32}$P-ATP. When this DNA was mixed with a 60-fold excess of unlabeled PvuII nuclease-digested pBR322 DNA and then ligated at the usual DNA concentration (10 μg/ml), the radioactivity behaved identically to the ethidium stain; the transition for both occurred at ca. 13% w/v PEG 6000 and the product distribution was identical. However, when the $^{32}$P-substrate was ligated by itself at much lower DNA concentrations (0.06 or 0.5 μg/ml), a broader transition occurred at ca. 9–10% w/v PEG 6000, the size of the linear products was definitely reduced, and there was some persistence of circular DNA products at concentrations above the transition. These results with the labeled preparations may be related to incomplete rephosphorylation in their preparation despite the use of a standard protocol for the labeling. The incomplete rephosphorylation is suggested by the relatively small proportion of closed circular DNA molecules made by the T4 DNA ligase as compared to the amount of nicked circular products (data not shown).

The relative concentrations of ATP and $Mg^{++}$ are important in maintaining the stimulation by PEG 6000 (and presumably by the other polymers as well) suggesting the need for a minimal concentration of $Mg^{++}$ that is unbound by ATP. Reducing the $Mg^{++}$ concentration from the usual level of 5 mM to 2.5 mM largely eradicated the massive stimulation of blunt-end ligation due to 15% w/v PEG 6000 (assayed at 0.5 mM ATP). Increasing the ATP concentration from the usual level of 0.5 mM to 1 mM also decreased that stimulation significantly and at 2 mM there was no stimulation at all (assayed at 5 mM $Mg^{++}$). On the other hand, decreasing ATP concentration ten-fold (to 0.05 mM) or increasing the $Mg^{++}$ four-fold (to 20 mM) did not affect the stimulation. We therefore suggest that caution be used if the ratio of $Mg^{++}$ to ATP is reduced from the suggested level either by changes in amounts of these materials or by the adventitious presence of $Mg^{++}$ chelators such as EDTA or nucleotide polyphosphates.

The effects of macromolecular crowding on blunt-end ligation appear to be correlated with an increase in the effective concentrations of the flush-ended DNA termini which are joined. The dependence upon high concentrations of background molecules and the lack of specificity with regard to these molecules is consistent with a volume-exclusion mechanism. In addition, the predominance of linear over circular DNA products when ligation occurs in high concentrations of background molecules also suggests a high effective concentration of DNA termini using statistical arguments. In contrast to the *E. coli* and rat liver enzymes, the T4 ligase can perform blunt-end ligation in the absence of background macromolecules-albeit at a relatively low rate—and under these conditions circular as well as linear products are formed. When this enzyme is assayed at higher macromolecule concentrations, the rate of blunt-end ligation increases and essentially only linear products are formed. Hence, the lack of circular products with the *E. coli* and rat liver enzymes is attributable to the requirement for a high background macromolecule concentration to allow detectable amounts of blunt-end ligation.

Polymer-stimulated ligation should be useful in a number of types of studies where it is desirable to increase the rate of ligation or the sizes of the products. It may be of help when ligating amounts of DNA or oligomers so low in concentration that reduced yields are obtained, or alternatively when preparing large amounts of polymers by ligation of oligomers or wherever very large amounts of DNA ligase might otherwise be required. Product distribution can be readily altered in favor of linear aggregates. Finally, polymer-stimulated joining may aid ligation which for convenience or other reasons is carried out under suboptimal or marginal ligase reaction conditions.

What is claimed is:

1. A method of enzymatically ligating DNA substrates comprising intermolecularly ligating between ends of said substrate or intramolecularly ligating two ends of one DNA molecule by a DNA ligase in the presence of a sufficiently high concentration of a non-specific, volume-excluding polymer which does not specifically interact with the DNA substrate, the DNA ligase or the DNA product, to obtain an increased ligation rate.

2. The method of claim 1, wherein the DNA ligase is T4 DNA ligase.

3. The method of claim 2, wherein the DNA substrate has blunt-ended termini.

4. The method of claim 1, wherein the ligase is rat liver nuclear DNA ligase.

5. The method of claim 1, wherein the ligase is *E. coli* DNA ligase.

6. The method of claim 1, wherein the DNA substrate is a DNA fragment comprising the digestion product of DNA and a DNA restriction enzyme.

7. The method of claim 1, wherein the DNA substrate is a complementary pair of deoxyribooligonucleotides at least eight base pairs in length.

8. The method of claim 7, wherein the DNA ligase is T4 DNA ligase.

9. The method of claim 1, wherein the DNA substrate is a mixture of a DNA fragment and a complementary pair of deoxyribooligonucleotides.

10. The method of claim 9, wherein the DNA ligase is T4 ligase.

11. The method of claim 1, wherein the volume-excluding polymer is polyethylene glycol polymer having an average molecular weight greater than about 2,000, a branched polysaccharide having an average molecular weight of about 70,000, or a natural protein.

12. The method of claim 1, wherein the polymer is a polyethylene glycol polymer having an average molecular weight of from about 6,000 to about 7,500.

13. The method of claim 12, wherein the polyethylene glycol polymer is present in a concentration of at least about 13% w/v.

14. The method of claim 1, wherein the DNA substrate has blunt-ended termini.

15. The method of claim 14 wherein the increase in ligation rate is 1,000 fold or greater.

16. The method of claim 1, wherein the DNA substrate has cohesive-ended termini.

17. The method of claim 16 wherein the increase in ligation rate is 10 to 100 fold.

18. The method of claim 1, wherein the non-specific polymer concentration is from about 5% w/v to about 45% w/v.

19. A method for preparing linear oligomers of duplex DNA comprising enzymatically ligating duplex DNA substrate end to end in the presence of a sufficiently high concentration of a non-specific volume-excluding polymer to promote intermolecular ligation.

20. The method of claim 19, wherein the non-specific polymer concentration is from about 5% w/v to about 45% w/v.

21. The method of claim 19, wherein the enzyme is a T4 DNA ligase, and the non-specific polymer is a polyethylene glycol polymer having an average molecular weight greater than about 2,000.

22. The method of claim 21, wherein the polyethylene glycol polymer has an average molecular weight of from about 6,000 to about 7,500.

23. The method of claim 22, wherein the polyethylene glycol polymer is present in a concentration of at least about 13% w/v.

24. The method of claim 19, wherein the duplex DNA substrate is a complementary pair of deoxyribooligonucleotides at least eight base pairs in length.

25. The method of claim 19, wherein the duplex DNA substrate comprises linear fragments of DNA.

26. The method of claim 19 wherein the size of resulting ligated DNA is 10 fold or greater.

* * * * *